United States Patent [19]

Chang et al.

[11] Patent Number: 4,620,044
[45] Date of Patent: Oct. 28, 1986

[54] HYDROLYSIS OF OLEFIN OXIDES TO GLYCOLS

[75] Inventors: Clarence D. Chang, Princeton; Stuart D. Hellring, Trenton, both of N.J.

[73] Assignee: Mobil Oil Corporation, New York, N.Y.

[21] Appl. No.: 787,931

[22] Filed: Oct. 16, 1985

[51] Int. Cl.$^4$ .............................................. C07C 35/14
[52] U.S. Cl. ...................................... 568/833; 568/832
[58] Field of Search ................................ 568/833, 832

[56] References Cited

U.S. PATENT DOCUMENTS 3,028,434  4/1962  Weiz ..................................... 568/833
4,560,813  12/1985  Collier ................................... 568/833

Primary Examiner—Werren B. Lone
Attorney, Agent, or Firm—Alexander J. McKillop; Michael G. Gilman; Marina V. Schneller

[57] ABSTRACT

Hydrolysis of olefin oxides to their corresponding glycols was catalyzed by a steam stable zeolite, in its acid form, characterized by a constraint index within the range of about 1 to 12. Conversions of olefin oxide, in the presence of water, proceeded with minimal catalyst degradation. The acidity of the zeolite enabled the use of milder conditions than generally applied for this hydrolysis with no loss of desired selectivity. In addition, the described procedure offered the advantages typically associated with a heterogeneous catalyst (e.g., ease of separation, use of fixed bed reactor, etc.).

18 Claims, 1 Drawing Figure

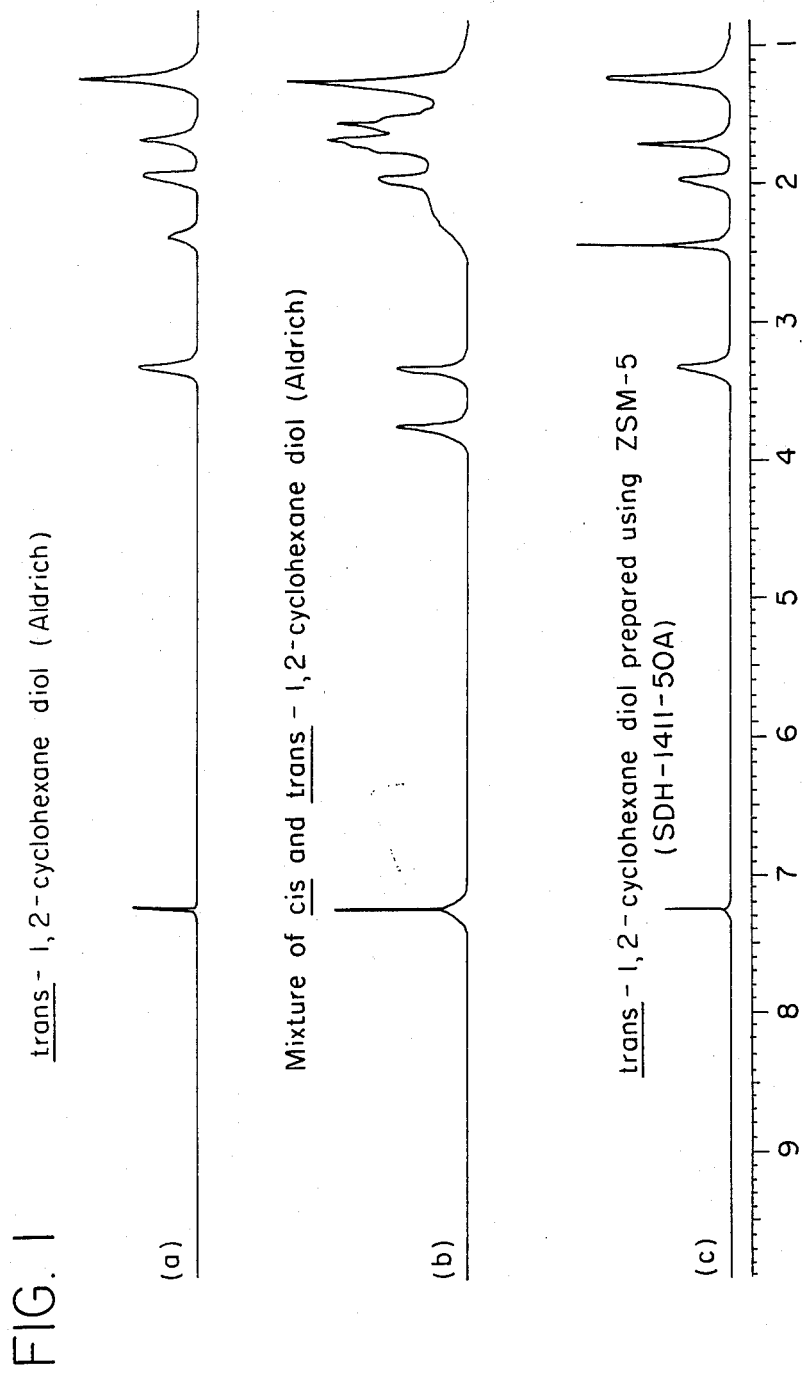

HYDROLYSIS OF OLEFIN OXIDES TO GLYCOLS

FIELD OF THE INVENTION

Olefin oxides, sometimes referred to as epoxides, are hydrolyzed to their corresponding glycols by using steam stable zeolites, having a constraint index within the approximate range of 1 to 12. The olefin oxide hydrolysis is effected under mild conditions with high product yield and selectivity.

BACKGROUND OF THE INVENTION

The hydrolysis of oxiranes to 1,2-diols is well known to be promoted by strong acid. As indicated in U.S. Pat. No. 3,028,434, prior commercial methods for producing ethylene glycol involved the reaction of ethylene oxide and water in the presence of sulfuric acid.

More recently, industrial processes for the catalytic conversion of ethylene oxide to ethylene glycol typically involve no catalyst. Absence of a catalyst is due to the difficulty incurred during the separation of homogenous acids, such as sulfuric acid or phosphoric acid, from the product mixtures. Presently, standard conditions employ a twenty molar excess of water over the oxide under batch conditions, of one hour residence time, at 150° to 204° C. and 200 psig. Selectivity of the industrial processes undertaken under the aforementioned conditions is reported as follows: ethylene glycol (88%), diethylene glycol (10%), triethylene glycol (2%), with a total glycol product of about 94.5%.

The objective of U.S. Pat. No. 3,028,434, was to provide an effective catalytic process for the manufacture of ethylene glycol by catalytic hydration of ethylene oxide in the presence of a solid catalyst characterized by high selectivity and high thermal stability. The solid catalysts described in the U.S. Pat. No. 3,028,434 were based on zeolite A and zeolite X. These zeolites suffered from the disadvantage of relative instability to steam, which was an inevitable component of the catalytic hydrolysis of ethylene oxide.

Ethylene and propylene glycols are produced in tremendous capacity throughout the world. A principle route to these materials involves the hydrolysis of the corresponding hypoxide. By significantly lowering the required temperature as well as shortening the residence time, in a catalytic conversion based on a steam stable catalyst, through put for a given plant can be increased.

SUMMARY OF THE INVENTION

Olefin oxides were hydrolyzed to their corresponding glycols when cofed with water over the proton form of zeolites. The use of steam stable zeolites permits the process to proceed with minimal catalyst degradation. The acidity of the zeolite enables the use of milder conditions than generally applied for this hydrolysis with no loss of desired selectivity. In addition, the described procedure offered the advantages typically associated with a heterogeneous catalyst, such as ease of separation, use of fixed bed reactor, etc.

DESCRIPTION OF THE DRAWINGS

FIG. 1(a), is the $^1$H-NMR (270 MHz) of trans-1,2-cyclohexane diol, (Aldrich).

FIG. 1(b) is the $^1$H-NMR (270 MHz) of a mixture of cis-and-trans-1,2-cyclohexane diol (Aldrich).

FIG. 1(c) is the $^1$H-NMR 270(MHz) of trans-1,2-cyclohexane diol prepared in Example 2.

DETAILED DESCRIPTION

The invention reveals a novel procedure to accomplish the facile hydrolysis of oxiranes to glycols. Although the use of faujasites to promote this hydrolysis has been described in U.S. Pat. No. 3,028,434, the faujasite materials required more severe reaction conditions and provide much lower yields than those found necessary with catalysts used in accordance with the invention. In addition, the former catalysts are known to further deactivate under steam conditions. By comparison, the catalysts used in accordance with the invention are relatively steam stable, exhibit high activity and selectivity.

The mild hydrolysis conditions which may be employed in accordance with the invention are attributable to the silicate or zeolite component of the catalyst employed. The silicate or zeolite ought to exhibit the following characteristics.

One characteristic which is requisite to usefulness of zeolites in the process of the invention is that the structure of the zeolite must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings do not generally appear to offer sufficient constraint to produce the advantageous hydrocarbon conversions, athough puckered structures exist such as TMA offretite which is a known effective zeolite. Also, such twelve-membered structures can be conceived that may be operative due to pore blockage or other causes.

Rather than attempt to judge from crystal structure whether or not a zeolite possesses the necessary constrained access, a simple determination of the "constraint index" may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted to between 550° F. (288° C.) and 950° F. (510° C.) to give an overall conversion between 10% and 60%. The mixture of hydrocarbons is passed at a 1 liquid hourly space velocity (LHSV), i.e., 1 volume of liquid hydrocarbon per volume of zeolite per hour, over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log \text{(fraction of n-hexane remaining)}}{\log \text{(fraction of 3-methylpentane remaining)}}$$

The constraint index approximates the ratio of the cracking rate constants for the two hydrocarbons. The ZSM-22 zeolite has a constraint index of about 7.3 at 800° F. (427° C.). Constraint Index (CI) values for some other typical zeolites are:

| Zeolite | C.I. |
| --- | --- |
| ZSM-5 | 8.3 |
| ZSM-11 | 8.7 |
| ZSM-12 | 2 |
| ZSM-23 | 9.1 |
| ZSM-38 | 2 |
| ZSM-35 | 4.5 |
| Clinoptilolite | 3.4 |
| TMA Offretite | 3.7 |
| Beta | 0.6 |
| ZSM-4 | 0.5 |
| H—Zeolon | 0.4 |
| REY | 0.4 |
| Amorphous Silica-Alumina (non-zeolite) | 0.6 |
| Erionite | 38 |

It is to be realized that the above constraint index values typically characterize the specified zeolites but that these are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables, such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is an approximation, taking into consideration the manner of its determination, with probability, in some instances, of compounding variable extremes.

While the above experimental procedure will enable one to achieve the desired overall conversion of 10 to 60% for most catalyst samples and represents preferred conditions, it may occasionally be necessary to use somewhat more severe conditions for samples of very low activity, such as those having a very high silica to alumina mole ratio. In those instances, a temperature of up to about 1000° F. and a liquid hourly space velocity of less than one, such as 0.1 or less, can be employed in order to achieve a minimum total conversion of about 10%.

The zeolite can be used in the hydrogen form. The hydrogen form of the zeolite, useful in the conversion processes is prepared, for example, by base exchanging the sodium form with, e.g., ammonium chloride or hydroxide whereby the ammonium ion is substituted for the sodium ion. The composition is then calcined at a temperature of, e.g., 1000° F. (about 540° C.) causing evolution of ammonia and retention of the hydrogen proton in the composition. Other replacing cations include cations of the metals of the Periodic Table, particularly metals other than sodium, most preferably metals of Group IIA, e.g., zinc, and Groups IIIA, IVA, IB, IIB, IIIB, IVB, VIB and Group VIII of the Periodic Table, and rare earth metals and manganese.

Ion exchange of the zeolite can be accomplished conventionally, e.g., by admixing the zeolite with a solution of a cation to be introduced into the zeolite. Ion exchange with various metallic and non-metallic cations can be carried out according to the procedures described in U.S. Pat. Nos. 3,140,251, 3,140,252 and 3,140,253, the entire contents of which are incorporated herein by reference.

The preferred zeolite satisfying the foregoing criteria is ZSM-5. The zeolite acidity as measured by, and expressed as, the alpha value, should range from 1 to 500 and preferably is 10 to 200.

The test for alpha value determination is described in a letter to the editor, entitled "Superactive Crystalline Alumino-Silicate Hydrocarbon Cracking Catalyst", by P. B. Weisz and J. N. Miale, *Journal of Catalysis*, Vol. 4, pp. 527-529 (August 1965) and in U.S. Pat. No. 3,355,078. The entire contents of both are expressly incorporated by reference herein. A procedure for determining the alpha value was more recently described in the Journal of Catalysis, Vol. VI, page 278-287, 1966, which is incorporated by reference herein. The manner of controlling the alpha value of ZSM-23 does not appear to be critical; that is, steaming the zeolite to the appropriate alpha value and/or control of mole ratio of Si:Al in the zeolite to control alpha value may be employed.

The catalyst composition comprising the zeolite may further include a support material which is matrix or binder component comprising a material resistant to the temperature and other process conditions.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee, Georgia and Florida clays or others in which the main mineral constituent is halloysite, kaolinite, nacrite or anauxite. Such clays can be used in the raw state as originally mined or initially subjected to calcination, acid treatment or chemical modification.

In addition to the foregoing materials, the zeolite employed herein may be composited with a porous matrix material, such as alumina, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel.

The process conditions for the catalytic hydrolysis of the olefin oxides are mild conditions. The olefin oxide, or epoxide, feed is aliphatic or cycloaliphatic; the aliphatic olefin oxide will contain at least 2 carbon atoms, and may contain up to 20 carbon atoms.

The catalytic hydrolysis is conducted in the presence of water (steam). Temperature of the catalytic hydrolysis may range from ambient temperature, at autogenous pressures up to 480, preferably the temperature range is from 25 to 100. The amount of water, based on moles of olefin oxide, will be in excess of the molar requirement for hydrolysis of the olefin oxide. Expressed in terms of molar ratio, the water to oxirane ratio can range from 2 to 50. Expressed as LHSV, in a continuous through put process, the aqua hourly space velocity of water (steam) can range from 1 to 100. As can be seen from the examples, elevated pressures need not be employed in the catalytic hydrolytic olefin oxide conversion of the invention. However, the process may be conducted at pressures ranging from subatmospheric to superatmospheric.

Conditions will be controlled depending on the reactivity of the olefin oxide subjected to the hydrolysis. The conversion of olefin oxides to glycols is exothermic. For example, a rapid increase in catalyst temperature will occur when the reactant is ethylene oxide, as the hydration of ethylene oxide to ethylene glycol is highly exothermic. Heat exchange or cooling means will ordinarily be used for the reactor which contains the catalyst f8 ethylene oxide conversion. Alternatively temperature control may be realized by diluting a gaseous feed stream with an inert gas.

The mild conditions which may be employed in the catalytic hydrolysis of olefin oxides to glycol allow for stereochemical selectivity of epoxide ring opening. That is, in the catalytic hydrolytic conversion of cyclohexene oxide, it was determined that the trans-glycol adduct was formed exclusively; that trans-glycol adduct is indicative of selective epoxide ring opening without further solvolysis of the product diol. Thus, in addition to high yields of products, the process of the invention can provide selectivity to pure stereochemical isomer(s).

EXPERIMENTAL

Typically no catalyst is applied in the industrial processes for oxirane conversions to glycols. This is due to the difficulty incurred during separation of homogeneous acids from the product mixtures. Standard conditions use a 20 molar excess of water over oxide under batch conditions (1 hr residence time), at 150–204° C. and 200 psig. Selectivity under these conditions is reported as follows: ethylene glycol (88%), diethylene glycol (10%), triethylene glycol (2%). Total glycol product was 94.5%. The following examples are illustrative of the invention.

EXAMPLE 1

Using ZSM-5 (H-form; 6 ml; $SiO_2/Al_2O_3=70$; $\alpha=190$), and cofeeding ethylene oxide (1 LHSV) with water (9 LHSV; 25 molar excess), gave 87% conversion to glycols under comparatively mild conditions (25° C.; 1 atm). The selectivity was roughly equivalent to that cited above: ethylene glycol (79%); diethylene glycol (15%), triethylene glycol (5%).

EXAMPLE 2

In another example, a solution of cyclohexene oxide (1.96 g; 20.0 mmol) in dioxane (10 ml) was added to a slurry of ZSM-5 (0.5 g) in water (1.0 ml; 55.6 mmol) and stirred overnight (room temperature). The catalyst was removed by filtration through Celite, and the reaction mixture concentrated in vacuo to yield 1,2-cyclohexane diol as a white powder (2.14 g; 92% yield). The product stereochemistry was shown to be exclusively trans by comparing the $^1H$ NMR spectra to that of an authentic sample (Aldrich) (FIG. 1). The trans product is indicative of selective epoxide ring opening without further solvolysis of the product diol. This is the expected product from such mild hydrolysis conditions.

What is claimed is:

1. A process for making 1,2-diols by the catalytic hydrolysis of an olefin oxide or a cyclo-olefin oxide, in the presence of water, comprising contacting the olefin oxide or a cyclo-olefin oxide of 2 to 20 carbon atoms with a catalyst comprising a silicate or zeolite, wherein said silicate or zeolite, has a contraint index of about 1 to about 12, wherein said silicate or zeolite has an alpha value ranging from 1 to 500; and wherein the silicate or zeolite contains acidic hydrogen atoms.

2. The process of claim 1, wherein the catalyst composition comprises ZSM-5.

3. The process of claim 1, wherein said contact is undertaken at a temperature ranging from 25° to 480° C. and at a pressure of 0 to 300 psig.

4. The process of claim 3, wherein said catalyst comprises ZSM-5 in the acid form.

5. The process of claim 1, wherein the water is present in a molar amount which is greater than the molar amount of said olefin oxide or said cyclo-olefin oxide.

6. The process of claim 3 wherein the water is present in a molar amount which is greater than the molar amount of said olefin oxide or said cyclo-olefin oxide.

7. The process of claim 4, wherein the water is present in a molar amount which is greater than the molar amount of said olefin oxide or said cyclo-olefin oxide.

8. The process of claim 1, wherein said olefin oxide is ethylene oxide.

9. The process of claim 4, wherein said olefin oxide is ethylene oxide.

10. The process of claim 7, wherein said olefin oxide is ethylene oxide.

11. The process of claim 1, wherein said cyclo-olefin oxide is cyclohexene oxide.

12. The process of claim 3, wherein said cyclo olefin oxide is cyclohexene oxide.

13. The process of claim 4, wherein said cycloolefin oxide is cyclohexene oxide.

14. A process for making trans-1,2-diols by the catalytic hydrolysis of an olefin oxide or a cyclo-olefin oxide, in the presence of water, comprising contacting the olefin oxide or a cyclo-olefin oxide of 2 to 20 carbon atoms with a catalyst comprising a silicate or zeolite, wherein said silicate or zeolite, has a constraint index of about 1 to about 12, wherein said silicate or zeolite has an alpha value ranging from 1 to 500; and wherein the silicate or zeolite contains acidic hydrogen atoms.

15. The process of claim 14, wherein the catalyst composition comprises ZSM-5.

16. The process of claim 14, wherein said contact is undertaken at a temperature ranging from 25° to 480° C. and at a pressure of 0 to 300 psig.

17. The process of claim 16, wherein said catalyst comprises ZSM-5 in the acid form.

18. The process of claim 14, wherein said cyclo-olefin oxide is cyclohexene oxide.

* * * * *